United States Patent
Bachmann

(10) Patent No.: US 7,060,080 B2
(45) Date of Patent: Jun. 13, 2006

(54) CLOSURE SYSTEM FOR SURGICAL RING

(75) Inventor: Michel Andre Bachmann, Vaux Sur Morges (CH)

(73) Assignee: Endoart S.A., PSE Ecublens (CH)

( * ) Notice: Subject to any disclaimer, the term of this patent is extended or adjusted under 35 U.S.C. 154(b) by 0 days.

(21) Appl. No.: 10/653,807

(22) Filed: Sep. 3, 2003

(65) Prior Publication Data

US 2005/0251181 A1  Nov. 10, 2005

(30) Foreign Application Priority Data

Sep. 4, 2002 (EP) .................................. 02019936

(51) Int. Cl.
*A61B 17/08* (2006.01)
(52) U.S. Cl. ..................... 606/151; 606/153; 606/157
(58) Field of Classification Search ........ 606/139–141, 606/153, 157; 600/37, 30, 31, 29; 24/23 EE, 24/20 EE, 284, 285; 128/100–111.1, 876; 604/909
See application file for complete search history.

(56) References Cited

U.S. PATENT DOCUMENTS

| | | | | |
|---|---|---|---|---|
| 2,163,048 A | * | 6/1939 | McKee ..................... 24/23 W |
| 3,840,018 A | | 10/1974 | Heifetz | |
| 4,118,805 A | | 10/1978 | Reimels | |
| 4,551,862 A | * | 11/1985 | Haber .......................... 600/30 |
| 4,592,355 A | * | 6/1986 | Antebi ....................... 606/144 |
| 4,753,086 A | * | 6/1988 | Schmidt ........................... 63/3 |
| 4,881,939 A | | 11/1989 | Newman | |
| 5,074,868 A | | 12/1991 | Kuzmak | |
| 5,226,429 A | | 7/1993 | Kuzmak | |
| 5,449,368 A | | 9/1995 | Kuzmak | |
| 5,601,604 A | | 2/1997 | Vincent | |
| 5,658,298 A | * | 8/1997 | Vincent et al. ............. 606/139 |
| 5,704,893 A | * | 1/1998 | Timm .......................... 600/29 |
| RE36,176 E | | 3/1999 | Kuzmak | |
| 5,938,669 A | | 8/1999 | Klaiber et al. | |
| 6,074,341 A | * | 6/2000 | Anderson et al. ............. 600/29 |

(Continued)

FOREIGN PATENT DOCUMENTS

FR  2823663  10/2002

(Continued)

*Primary Examiner*—Glenn K. Dawson
*Assistant Examiner*—Michael G. Mendoza
(74) *Attorney, Agent, or Firm*—Nicola A. Pisano, Esq.; Luce, Forward, Hamilton & Scripps LLP

(57) ABSTRACT

A surgical ring (1) designed to be implanted around (a) biological organ(s), the ring (1) being formed by a flexible band (2) including a first and second extremity (3, 4), the flexible band (2) being designed to be closed near its two extremities (3, 4) by a closure system so as to form a closed loop featuring an internal contact surface (2A) external 10 surface (2B). The closure system includes a means of encircling (5) that is integral with the first extremity (3) and arranged to evolve between a de-latching configuration, where the means of encircling (5) forms an open collar freeing the second extremity (4), and a latching configuration where the means of encircling (5) forms a closed collar designed to surround the second extremity (4) so as to unite it with the first extremity (3), the closed collar having opposite front (6) and rear (7) faces, between which an encircling opening extends that is designed to accept the second extremity (4).

29 Claims, 2 Drawing Sheets

U.S. PATENT DOCUMENTS

| | | | |
|---|---|---|---|
| 6,090,131 A * | 7/2000 | Daley ........................ | 606/219 |
| 6,102,922 A | 8/2000 | Jakobsson et al. | |
| 6,511,490 B1 | 1/2003 | Robert | |
| 6,547,801 B1 * | 4/2003 | Dargent et al. ............. | 606/157 |
| 2003/0073880 A1 | 4/2003 | Polsky et al. | |

FOREIGN PATENT DOCUMENTS

| | | |
|---|---|---|
| WO | WO 01/49245 | 7/2001 |
| WO | WO2003105732 | 12/2003 |
| WO | WO2004019671 | 3/2004 |

* cited by examiner

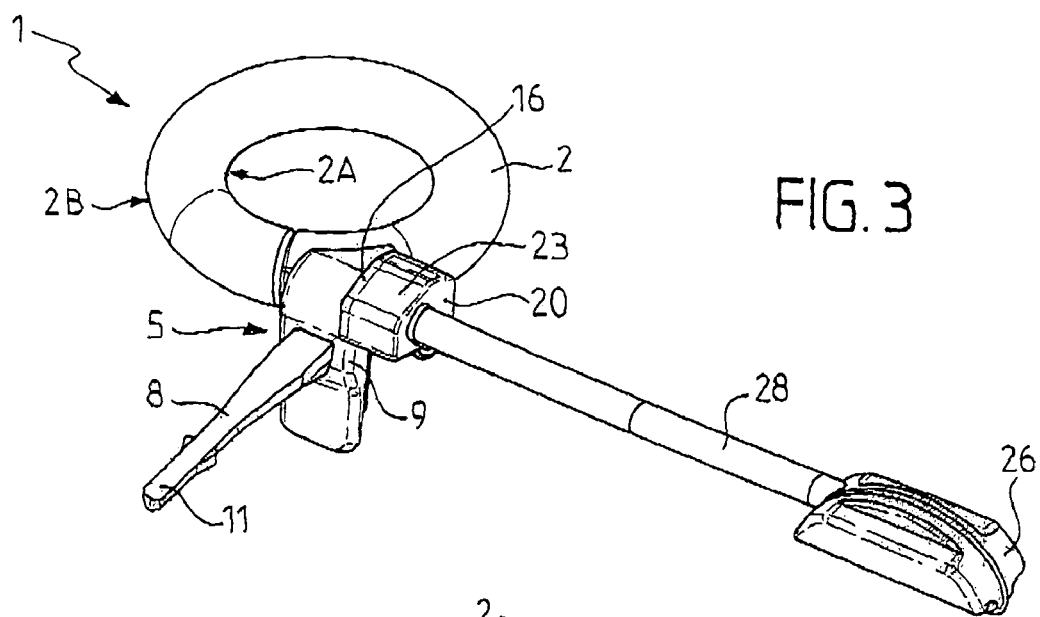
FIG. 3
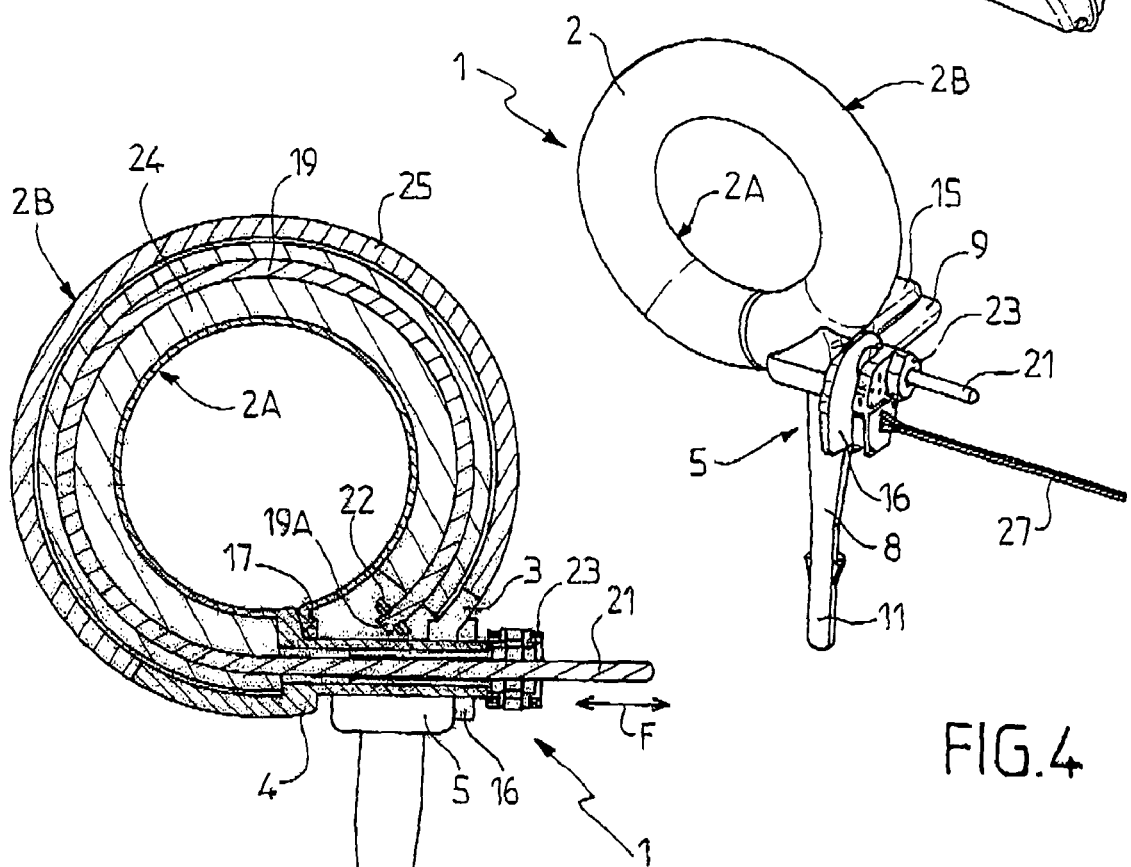
FIG. 4
FIG. 5

CLOSURE SYSTEM FOR SURGICAL RING

CROSS REFERENCE TO RELATED APPLICATIONS

This application claims priority to European Patent Application No. EP-02 019936.0, filed Sep. 4, 2002.

FIELD OF THE INVENTION

The present invention relates to the technical domain of surgical implants designed to be implanted in the body of a patient, around (a) biological organ(s) having a pouch or a duct; and, more specifically, gastric rings designed to treat obesity by implantation of a flexible gastric ring, designed to form a closed loop around the stomach in order to reduce the diameter of the opening of the stoma.

The present invention involves a surgical ring designed to be implanted in the body of a patient, around (a) biological organ(s) having a pouch or duct, in order to modify the passage cross-sectional area of said organ(s) when it is constricted by the ring. Said ring consists of a flexible band, consisting of a first and second extremity. Said flexible band is designed to be closed towards these two extremities by a closure system, in order to form a closed loop. Said closed loop features an internal contact surface with the biological organ and an opposite external surface.

More specifically, the invention involves a gastroplasty ring, but it may also involve a ring designed to be used to treat urinary or fecal incontinence (artificial sphincter), or even a ring designed to regulate blood flow in, for example, blood vessels; this list is by no means exhaustive.

BACKGROUND OF THE INVENTION

Surgical intervention is already known in patients afflicted with extremely severe obesity (morbid obesity), i.e. in the case of patients whose weight exceeds, for example, the ideal weight of at least 50 kg, by implanting gastroplasty rings in such patients. Such interventions not only allow a number of serious health problems resulting from such overweight to be avoided, but also, and especially, the certain and premature death of these patients can be avoided as well.

It is well known that patients suffering from morbid obesity experience a significant decrease in life expectancy, of at least ten to fifteen years, all the while suffering from significant psychological problems.

Moreover, a whole series of related health phenomena are implicated with this problem, such as cardiovascular troubles, hypertension, diabetes, and even severe arthritis.

It is also well known that, for such patients, treatments based on strict diets combined with a series of physical exercises, also associated with changes in behavior, specifically in nutrition, are generally poorly adapted, even if these treatment methods are acknowledges as being the most healthful.

This is the reason for which effective, long-term treatments for morbid obesity involve surgical intervention.

Generally speaking, we distinguish surgical treatment techniques involving a flaw in nutritional absorption, i.e. a shortening of the passage of foodstuffs and digestive successes, and techniques involving use of a gastric restriction that reduces the size of the stomach.

Surgical techniques involving a flaw in absorption are those involving, for example, a "by-pass" technique, or a bypass of the small intestine, or even techniques making use of a separation of the passage of foodstuffs relative to digestive successes.

These surgical techniques are relatively drastic and may give rise to severe complications, and this is the reason for which they are hardly ever used any more.

The tendency now is, in fact, to use surgical techniques implementing surgical interventions that are less drastic, such as gastric restriction involving placement of a gastric ring.

These techniques are now in common use, and for the most part make use of, as described for example in document WO-94/27504, a flexible band designed to be implanted around the stomach, forming a closed loop defining a fixed, pre-established ring parameter, thanks to a closure system. Against the surface that is intended to come into contact with the stomach, the body of the flexible band features, a variable-volume inflation chamber, which is linked to an adjustment catheter. This catheter allows injection or withdrawal of a fluid in the compression chamber, so as to vary the internal perimeter of the loop. This allows the diameter of the stoma to be changed or adjusted. In this way, in combination with the fixed, pre-established diameter of the ring, it is possible to regulate, however slightly, the diameter of the ring. This allows adjustment of the diameter of the stoma, and therefore adjustment of the quantity of foodstuffs ingested.

The closure system described in document WO-94/27502 makes use of a socket that is integral to one extremity of the flexible band. The opening of said socket extends tangentially from the ring and is shaped to cooperate with a profiled head that is integral to the second extremity of the flexible band, so that said head may be deformed in order to pass through the opening of the socket and create a thrust block against the edges of the socket, thus closing the ring with a latch closure.

Such a closure system has been shown to be impractical to implement during the latching operation of the ring around the patient's stomach.

In fact, in order to bring this operation to a satisfactory completion, the surgeon finds himself obligated to make special traction efforts in a direction tangential to the ring, corresponding to the direction in which the opening of the socket extends, in order to bring the head to cooperate with the socket. This effort's tangential direction corresponds, for the surgeon, to manipulations that are distinctly against and parallel to the stomach wall, which turns out to be difficult for the practitioner and risky for the patient, because it increases the risk that the practitioner will accidentally damage the stomach.

Moreover, in order to proceed with latching the ring, the surgeon finds himself restricted to blocking the extremity of the flexible band that has the socket, and to bring this extremity together to the second extremity featuring the head, then to engage the head in the socket by pulling directly on the second extremity, like for a sliding knot, until the latch engages by flexible joint Thus, a risk exists that the surgeon might exert a traction force on the second extremity that is too hard, which would lead to damaging of the flexible band that forms the ring.

The drawbacks indicated above are exacerbated by the fact that the contoured head is lengthened by the diameter-adjustment catheter, which complicates the closure procedure even further, and which could lead to damage to the catheter.

Also, devices from within the prior art, such as that described in application WO-94/27504, have been shown to have drawbacks related to the difficulty in carrying out any surgical intervention which could come about after the gastroplasty implant.

In fact, it has been shown that, despite the possibility of changing, within certain limits, the diameter of the ring without surgical intervention, the installation of such gastric implants may sometimes be accompanied by intolerance phenomena, for example, vomiting linked to too great reduction in the diameter of the stoma, or even an ineffective action of the implant, linked to too great a diameter of the stoma, or yet again just a constraint, infection, or local or general inflammation.

This is the reason for which, in this case, it is necessary to intervene once again surgically, either to relieve the patient, or to adjust or change the gastroplasty ring that was previously implanted.

Such surgical interventions are particularly complex, and require complete opening of the ring, so as to change and replace it.

Standard system closures do not permit easy opening of the ring, for reasons similar to those leading to drawbacks encountered during closure of the ring.

Since that time, such post-implantation surgical interventions often lead to cutting of the ring by the surgeon, so as to change and replace it.

Finally, latching or unlatching of standard rings is therefore carried out by exerting opening or closing force, of a type like a traction force, directly on the flexible band itself. Such forces, generally exerted with the help of competing instruments, such as surgical pincers, may cause damage to the ring (tearing, piercing . . . ) which could render the ring non-functional.

The risk of occurrence of such problems is accentuated by the awkward opening/closing gesture required by such standard devices.

Moreover, implementation of a standard opening/closing system is particularly delicate, if not impossible, in the case of a ring whose diameter is controlled by an activating device making use of an actuator, of the type with an electric motor fitted to the flexible band that forms the ring. In fact, the rigidity of the motor block and its relative bulk prohibit all principles of opening or closing based on threading of one extremity of the flexible band into the other extremity, and/or a flexible connection of one extremity into the other.

OBJECTS AND SUMMARY OF THE INVENTION

The invention consequently seeks to rectify the various drawbacks listed above, and to propose a new surgical ring, specifically a gastric ring, which offers a closing system whose implementation reduces the mechanical constraints applicable to the flexible band forming the ring during installation and use of the ring, and which would be particularly practical and reliable.

Another object of the invention proposes a new surgical ring, specifically a gastric ring, featuring a closure system that would be particularly simple and low-cost.

Another object of the invention proposes a new surgical ring, specifically a gastric ring, featuring a closure system that is particularly efficient.

Another object of the invention proposes a new surgical ring, specifically a gastric ring, designed to ease manipulation of the ring during installation, as well as during any future re-opening and re-closing of the ring.

Another object of the invention proposes a new surgical ring, specifically a gastric ring, featuring a closure system that is particularly reliable.

Another object of the invention proposes a new surgical ring, specifically a stomach ring, that is particularly atraumatic for the patient and well tolerated by the patient.

Another object of the invention proposes a new surgical ring, specifically a gastric ring, which is particularly sturdy, compact and easy to manufacture.

Another object of the invention proposes a new surgical ring, specifically a gastric ring, whose closure system is particularly well adapted to the presence of an actuator, designed to generate a variation in the internal perimeter of the ring, and mounted on one of the extremities of the flexible band constituting said ring.

The designated objects of the invention are achieved with the help of a surgical ring, designed to be implanted in the body of a patient around (a) biological organ(s) comprising a pouch or a duct, in order to modify the cross-sectional area of the passage of said organ when it is tightened by the ring, said ring being formed by a flexible band comprising a first and second extremities, said flexible band being designed to be closed with the two extremities by a closure system that forms a closed loop, said closed loop having an internal surface in contact with the biological organ and an opposing external surface, characterized in that the closure system features a means of encircling that is united to the first extremity and arranged so as to evolve between:

an unlatching configuration where the means of encircling forms an open collar freeing the second extremity, and a latching configuration where the means of encircling forms a collar designed to surround the second extremity, so as to unit it with the first extremity, said closed collar having opposite front and rear faces between which extend an encircling opening designed to receive the second extremity.

BRIEF DESCRIPTION OF THE DRAWING

Other objects and advantages of the invention will become more apparent upon reading the attached description, as well as with the help of the attached drawings, which are solely for illustration and information purposes, in which:

FIG. 3 shows, in a perspective view, the stomach ring shown in FIGS. 1 and 2. Said ring is equipped with a receiving antenna, with a view to long-distance control of the actuator.

FIG. 4 represents, in a perspective view, a detail of the ring actuator shown in FIG. 3.

FIG. 5 shows, in longitudinal section view, the ring shown in FIGS. 3 and 4.

MORE DETAILED DESCRIPTION

Figure 1:
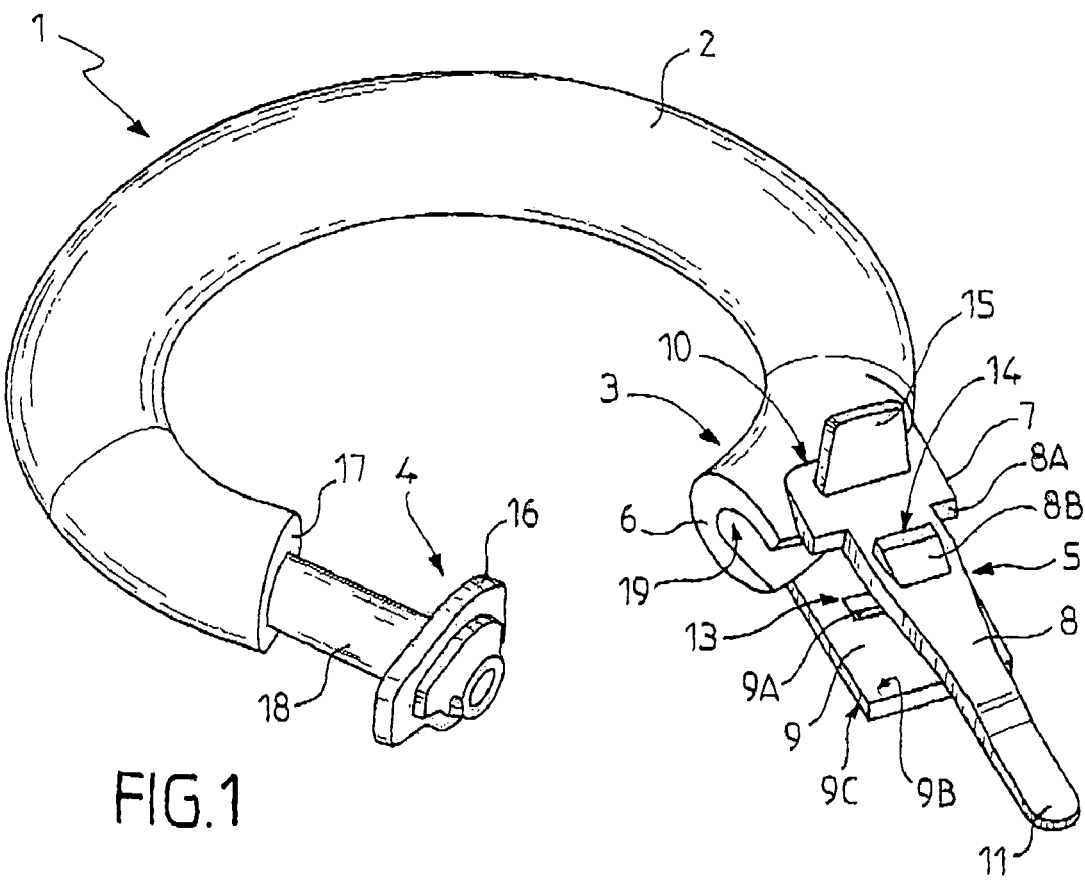
FIG. 1 shows, in a perspective view, an example of embodiment of a surgical ring in compliance with the invention, shown open.

In the following description, reference will be made, solely as an example, to a stomach ring designed to be implanted around the stomach in order to reduce the diameter of the opening of the stoma or around the esophagus.

In effect, the invention is in no way limited to this application, and its purpose is, on the contrary, to cover other surgical rings, such as those used to treat urinary or fecal incontinence, or those around blood vessels to control blood flow.

In the case of treatment of urinary incontinence, the ring will be implanted around the bladder or urinary tracts, and in the case of treatment of fecal incontinence, it will be implanted around gastrointestinal tracts and specifically around anal structures of the intestine.

FIGS. 1 through 5 illustrate a gastric ring 1 in compliance with the invention, designed to be implanted in the body of a patient around the stomach, in order to modify the passage area of the stomach, i.e. carry out a gastric restriction by reducing the diameter of the opening of the stoma when it is tightened by the ring.

Gastric ring 1, in compliance with the invention, is shown in the form of a flexible band 2, preferably tubular, whose flexible and elastic envelope features a smooth surface 2A and 2B, such that it is easily tolerated by the patient and by the stomach tissues. Band 2 is made, for example, of elastomeric material, of the silicone type.

Flexible band 2 features a first extremity 3 and a second extremity 4. The flexible band 2 is designed to be closed at its two extremities 3 and 4 by a closure system which forms a closed loop, as shown in FIGS. 2 through 5.

In a variation of the embodiment shown in the figures, gastric ring 1 incompliance with the invention is shown in the shape of a torus of revolution, for example of substantially circular cross-section, which is bounded on its exterior by a single- or multiple-layer envelope, which could ideally form a protective covering, for example based on or made of silicone.

The closed loop made by flexible band 2 features an internal surface 2A, in contact with the biological organ, under the circumstances the stomach, and an opposite external surface 2B.

According to the invention, the closure system of flexible band 2 comprises a means of encircling 5, mounted integral to the first extremity $. Said means of encircling 5 is implanted and in compliance with said first extremity 3, in order to evolve between:
  a latch configuration (see FIG. 1) where the means of encircling 5 forms an open collar, freeing the second extremity, i.e which has no maintenance interaction with said second extremity.
  a latch configuration (see FIG. 2) where the means of encircling 5 forms a closed collar designed to surround the second extremity, so as to join it with the first extremity. Said closed collar features a front face 6 and an opposite rear face 7, between which an encircling opening extends, designed to receive the second extremity 4 of the ring.

Ideally, the encircling means 5 is arranged to pass reversibly between the latching configuration shown in FIG. 1 and the latching configuration shown in FIGS. 2 through 5.

In this way, the user may open or close the ring at will, without changing the ring's functionality in any way whatsoever.

In particular, the reversible nature of the means of encircling is of an intrinsic nature, i.e. it allows said means of encircling to pass from its latching configuration to its unlatching configuration without the need to destroy or permanently break any element whatsoever of the latching device.

Likewise, this intrinsic reversible nature allows said means of encircling to pass from its unlatching configuration to its latching configuration without need to implement any distinct exterior latching element of the means of encircling.

It is, nevertheless, perfectly plausible that the means of encircling is not designed for a single usage, and that it not, for example, be able to pass more than one single time from the unlatched to the latched position, where the inverse operation would require a more or less partial alteration in ring 1, still without deviating from the scope of the invention.

Ideally, the means of encircling 5 consists of a male element 8 and a female element 9, both of which are mounted integrally to the first extremity 3 of the ring, and mounted on or close to the latter in such a way that, at the time they are connected, the means of encircling 5 is latched, forming the closed collar.

Thus the means of encircling 5 allows the tightening of the second extremity 4 to the first extremity 3, in loop fashion. After this, we understand that the general concept of the invention is opposed to the standard latching concept.

In effect, in the standard manner, the active latching means were distributed on each extremity of the flexible band, such that the forces applied for latching or unlatching were exerted directly on the flexible band, with all the drawbacks this may entail.

On the contrary, the invention allows us to carry out latching of the ring without exerting noticeable pilling force on the flexible band, because the main elements of the latching system requiring an external activation are all arranged on the same extremity of the flexible band, and are not divided between the two extremities.

Preferably, the female element 9 comprises an opening 9A traversing the thickness of female element 9, between a first side 9B and a second opposite side 9C. As for male element 8, it comprises, preferably, a tab designed to be slid into orifice 9, said tab featuring a means of blockage 8A and 8B arranged to cooperate with female element 9, and more specifically with orifice 9A.

Preferably, tab 8 extends from the exterior surface of the ring on the level of the first extremity 3, in a substantially longilineal manner, and thus featuring a link extremity 10, attached to the external surface of ring 1, and a free extremity 11.

The female element 9 is also attached to the external surface of the ring, with regard to tab 8, and extends in a substantially longilineal way parallel to tab 8, and is separated from tab 8 by the diameter, or thickness, of flexible band 2.

Ideally, tab 8 and female element 9 are oriented so that the closed collar extends towards the exterior of ring 1, so that the closure system slopes in order to facilitate manipulation by the practitioner.

The opening of the encircling, as defined by the closed collar thus lies in a plane which, ideally, forms an angle that is substantially oblique relative to the corresponding radial direction, it being understood that it is perfectly possible that said plane may extend radially relative to the main axis of symmetry of the ring.

Preferably, tab 8 comprises, on the one hand, a first means of support 8A, which forms the first means of blockage, and is designed to be supported against the peripheral edge 13 of orifice 9A on the first side 9B of female element 8. On the other hand, tab 8 comprises a second means of support 8B, which forms a second means of blockage, and is designed to be supported against the peripheral edge of orifice 9A on the second face 9C of female element 9. The second support means 8B is in shaped to cooperate with orifice 9A, like a cam in a thrust bearing. In other words, the second means of support 8B is arranged so that it can pass completely through orifice 9A, all the while having an anti-recoil means that keeps it from spontaneously going in the opposite direction, thus creating the ring latch. This cam-thrust system may be of a reversible nature, i.e. allow the deactivation of the cam's anti-recoil feature consisting of the means of support 8B. The first and second means of support, 8A and 8B, ideally, are arranged relative to each other so that, in latch configuration (shown in FIGS. 2 through 5), they tighten female element 9 between them, so as to ensure a stable latching configuration, where no significant variation of the internal perimeter of the closed collar is allowed.

Ideally, tab 8 and female element 9 are both in the shape of a flexible strip and made of a flexible material like an elastomer.

Said tab 8, as shown in the figures, extends from its link extremity 10 according to a T-like shape. The juncture between the small leg and the large leg of the T correspond to a shoulder. This shoulder defines a support surface 8A, forming a first support means. The large leg of the T should ideally have a chamfer profile, to facilitate its introduction and passage into orifice 9A. The part of tab 8 that forms the large leg of the T also comprises a flexible extension 8B, which forms a second means of support. This flexible extension 8B features an inclined surface, forming a ramp which allows its easy introduction into orifice 9A. Said inclined surface is interrupted by a flat surface 14, which is substantially perpendicular to the body of tab 8, said flat surface acting as a second means of support.

Ideally, the free extremity 11 of tab 8 is shaped to act as a first prehension support, which, by seizing it, allows us to pass tab 8 and flexible extension 8B through orifice 9A to make this closed collar.

Ideally, the ring according to the invention comprises a second prehension support 15, which allows the user to keep the male element consisting of tab 8, when he manipulates female element 9, so as to proceed with the separation of the male and female elements, in order to open ring 1. Said second prehension support 15 extends, ideally, substantially outwards of ring 1 and perpendicularly to tab 8 and, starting from tab 8, in proximity to the extremity of link 10.

Ideally, female element 9 comprises a third prehension support, which eases separation of male element 8 and female element 9, for purposes of opening ring 1. Preferably, as shown in the figures, the body of female element 9 is shaped so that it itself forms said third prehension support.

The male-female latching system described above is not of course the only possibility within the scope of the invention, and we could substitute any other means of closure that is well known to the craftsman, by implementing, for example, a "frog" closure, Velcro strips or even a pants-belt type of closure, without deviating from the scope of the invention.

Moreover, if up to now we have described a means of encircling consisting of two connectable sides which form a closed collar, it is conceivable, without deviating from the scope of the invention, that the means of encircling could be made of a collar in the shape of a permanent buckle, but whose internal perimeter is adjustable by any means known, in order, specifically, to reach a dimension that is sufficiently large, relative to the dimension of the transverse section of the second extremity 4, so as to free this second extremity 4 from all mechanical constraints, notably friction or tightening.

Ideally, the second extremity 4 of ring 1 features a first stopping means 16, designed to thrust against the rear side 7 of the closed collar surrounding the second extremity 4 of the ring, when the ring is in the latching configuration, so as to prevent shifting, by sliding or slipping, of the second extremity 4, in the direction of ring 1's opening, i.e. in the direction of expansion of the internal perimeter of said ring 1.

The invention notably also proposes to protect the technical concept of a surgical ring whose closure system associates, on the one hand, a means of encircling which forms an open or closed collar, with, on the other hand, at least one means of stopping designed to ensure latching according to a defined perimeter of the ring.

Ideally, the second extremity 4 of ring 1 is also provided with the second means of stoppage 17, designed to be thrust against the front face 6 of the closed collar surrounding the second extremity 4 of the ring in the latching configuration, so as to prevent shifting of the second extremity 4 in the direction of ring 1's closure, i.e. in the direction of a restriction of the internal perimeter of said ring 1.

Preferably, said first and second means of stopping 16, 17 are arranged relative to each other along the terminal portion of ring 1, corresponding to the second extremity 4, in order to tighten the closed collar between themselves in latching configuration, so as to substantially prevent any shifting of the second extremity 4 relative to the first extremity.

The combination of the means of encircling 5 and the first and second means of stoppage 16 and 17 thus allows us to unite the first extremity 3 with Z the second extremity 4, both from the radial and tangential points of view, relative to the main axis of symmetry of ring 1.

Figure 2:
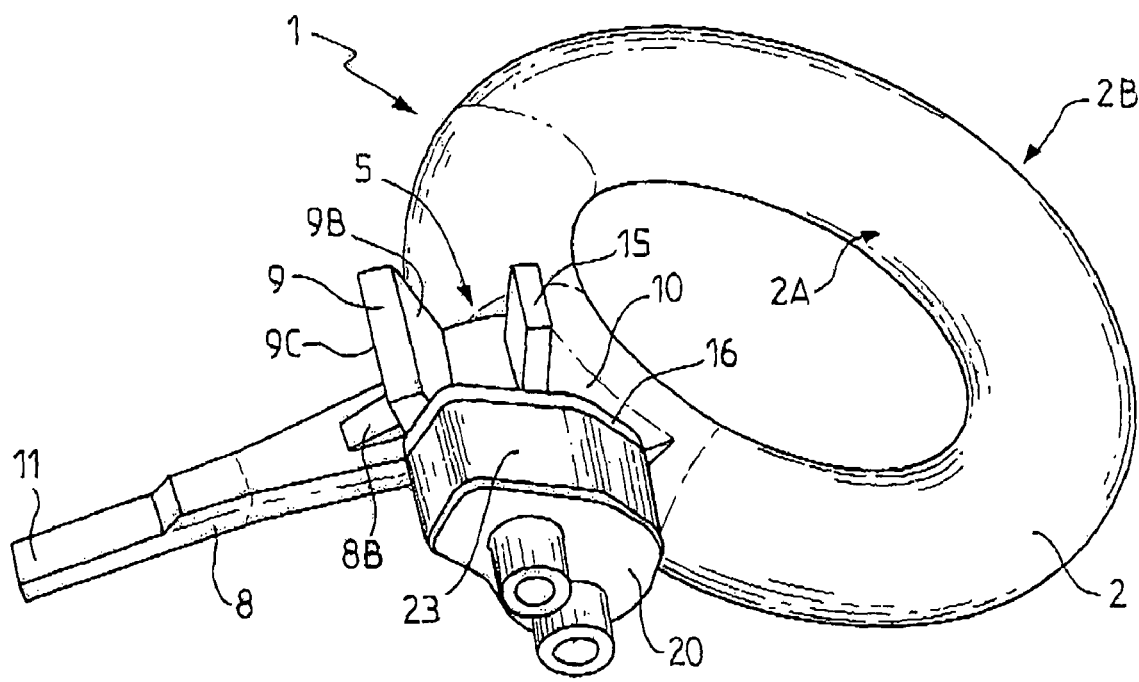
FIG. 2 shows, in a perspective view, the surgical ring shown in FIG. 1, in a closed position and fitted with an actuator.

Ideally, flexible band 2 features a portion of reduced section 19 on the level of the second extremity 4 of ring 1. Said portion is designed to be lodged laterally into a recess 19B, of a substantially complementary shape, arranged at the level of the first extremity 3 within the body of ring 1. Said recess 19B is positioned in the continuity of male element 8 and female element 9, so as to make a U shape, where the legs of the U are made, respectively, by tab 8 and female element 9, whereas the heart of the U consists mostly of recess 19B. Said recess thus forms a part of the closed collar in latching configuration, which allows us to assure a continuity of the internal surface 2A of the ring when the ring is in the closed position, as it is shown in FIG. 2. The internal surface 2A of ring 1 is thus regular and continuous, and presents no nibs or discontinuities at the level of the juncture of extremities 3 and 4, which guarantees that the ring is perfectly atraumatic.

Ideally, flexible band 2 features a shoulder 17 at the level of transition of the reduced-section portion 18, said shoulder 17 acting as a second means of stopping. Thus, the ring according to the invention has a particularly compact nature in the closed position, as is indicated in FIG. 2.

Preferably, flexible band 2 and closure system 5 form a single piece, of two components made from elastomeric materials of different hardnesses, so as to adapt them to the specific mechanical constraints they will be subjected to during opening/closing of the system.

As a variation, the flexible band 2 and the closure system 5 may be made as a single-piece unit, ideally made of a single material.

Ideally, and in compliance with the variations in production shown in the figures, ring 1 according to the invention consists of a system that reversibly controls the variation of its internal perimeter (corresponding to internal surface 2A), said system consisting of a flexible filiform element 19 having good flexibility and good mechanical resistance, inserted longitudinally and by sliding along the principal axis of symmetry of the main cylinder or body of ring 1. Said element 19 occupies the cavity linking the first and second extremities 3 and 4, and sensibly extends between said first and second extremities 3 and 4, i.e. sensibly along the entire developed length of ring 1.

As illustrated in FIG. 5, the filiform flexible element 19 is mounted so as to define a fixed portion 19A, which is united using a uniting means 22, which make use for example of a retaining ring and a washer, or any other equivalent means, with the first extremity 3 of ring 1. The other extremity portion of the filiform flexible element 4 forms a free portion 21, i.e. one which can be shifted by translation relative to the fixed portion 19A. Said free portion 21 is functionally associated with an actuator 23, mounted in ring 1 even near or on the level of the second extremity 4. The function of actuator 23 is to transmit the energy necessary, to ensure, when it is activated, the reversible translation of the filiform flexible element 19 inside the ring, i.e. the reversible displacement of the free portion 21 relative to the fixed portion 19A, so as to obtain an associated variation of the internal perimeter of ring 1, i.e. an increase or reduction of its internal diameter.

Thus, directly mounting actuator 23 on one of the extremities 4 of the ring allows significant gain in space, and a good mechanical efficiency.

Ideally, the free portion 21, which extends, for example, on an order of a few centimeters, or along the whole length of the flexible filiform element, is provided with a means of force cooperation, designed to assure transmission of the energy supplied by actuator 23 to all of the flexible filiform element 19 starting from its point of support, the fixed portion 19A.

Ideally, the means of force cooperation are made using a screw thread pitch.

According to the invention, flexible filiform element 19 has sufficient flexibility so that it can adapt itself to the substantially circular shape of the ring, while also being able to transmit the force necessary to adjust the ring's diameter. Ideally, the flexible filiform element 19 is made of a flexible core, preferably metallic, for example of circular cross-section, on which is fixed, and coaxially rolled, for example along its whole length, at least one unjointed coil spring which forms the screw thread pitch.

In a particularly ideal way, flexible filiform element 19 consists of two unjointed coil springs to form the screw thread pitch, respectively, a first spring, rolled helicoidally all along the flexible core, and a second spring, of greater exterior diameter, and preferably consisting of coils of rectangular transversal section, so as to delineate a flat external generatrix, said first spring being interposed between the coils of the second spring so as to maintain a constant square screw thread pitch.

Thanks to this arrangement, it is now possible to consistently keep a feed that is substantially constant and efficient, even in the case of deformation of the flexible filiform element 19. This confers a great precision and effectiveness to the device, while at the same time it has the energy efficiency necessary for it to function, because of the high efficiency of the transmission by a square feed screw.

Thanks to this arrangement, it is possible to guarantee a stable adjustment position even when no energy is provided to the system.

The second spring may ideally be obtained by laser cutting of a hollow cylindrical tube It is mounted on and between the coils of the first spring using longitudinal traction. The second spring is therefore naturally endowed with an intrinsic elastic compression force which tends to impart an engaging force on the coils. This intrinsic force is then thrown down by the coils of the first spring, against which they are supported. In this way we obtain a constant step in spite of the natural and indispensable elasticity and flexibility of the elongated flexible element.

Actuator 23 may be made using any standard method well known to the craftsman which is likely to work with the screw thread pitch to transmit movement to it. In a particularly ideal way, actuator 23 may be provided with a simple nut screw which would allow us to ensure drive action of the screw thread pitch, where actuator 23 could in general be a motor, of electric, electromagnetic or other type, without deviating from the scope of the invention.

Preferably, the actuator is mounted on ring 1 to constitute the first means of stoppage 16, or at least to be associated with it.

Preferably, as shown in the figures, the actuator is mounted between a first and second parallel flange 16 and 20 (the second flange 20 is not illustrated in FIG. 1, 4 or 5). Said first flange 16 constitutes the first means of stoppage.

As a variation of embodiment not shown in the illustrations, it is of course possible to replace the screw thread pitch described previously by any equivalent technical means, and for example a meshing rack on an actuator 23 fitted with a gear or an equivalent means. We could also propose the production of the flexible filiform element 19 in the shape of a simple cable, driven reversibly by actuator 23 by means of a pulley.

As shown in the figures, gastric ring 1 in compliance with the invention consists, generally, of a main body 24 based on a compressible material, and which fills the interior of the envelope. In this compressible material 24 is inserted longitudinally and, substantially, with the possibility of sliding, the flexible filiform element 19, as shown, for example, in FIG. 5.

In a particularly ideal way, compressible material 24 is ePTFE, whose compressibility and stability in constriction are particularly well-suited to this type of application.

According to a variation of embodiment (not shown in the illustrations), the ring according to the invention consists of an invention of silicone material and of substantially constant thickness, which makes up the watertight exterior covering of the ring. The interior of the ring is made exclusively of compressible material 24, for example ePTFE, inside which the flexible filiform element 19 is inserted with slight clearance.

The first extremity 3 comprises a pouch, for example filled with glue, and in which is mounted and fixed the fixed part 19A, with means of uniting 22.

According to this first variation of the embodiment, the action of the actuator 23 on the flexible filiform element 19 transmits an actuating force according to one of the directions indicated by arrow F illustrated in FIG. 5, which in consequence compresses or releases, longitudinally, the compressible material 24, which translates, by a variation associated with the diameter of the ring, both internal and external, to the manner of a sliding knot.

Another variation of the embodiment, illustrated in FIG. 5, does not differ from the preceding one except in the specific arrangement of the external envelope whose dorsal periphery 25 is reinforced so as to flange the external radial extension or centrifuge of the ring which, on the contrary, favors the internal radial or centripetal variation of the ring diameter. In this way, we favor the radial variation of the ring diameter at its internal periphery, which is opposite its dorsal periphery.

As it is shown, the reinforced dorsal periphery 25 may be implemented in the form of an external envelope, of which only the dorsal periphery features an oversize, i.e. an external dorsal thickness that is greater than the rest of the external envelope (FIG. 5). Alternatively, or complementarily, the dorsal periphery 25 may also be made using a polymeric material of greater hardness than that of the rest of the polymer-material envelope. It is also possible to include, inside reinforced dorsal periphery 25, a reinforcing insert, preferably metal, extending over the majority of the periphery of the ring between compressible material 24 and the dorsal periphery 25. Ideally, the insert may feature a shape memory that is substantially circular, in order to achieve a circular elastic rest position of the ring.

Thanks to this arrangement, the increase or the reduction in diameter of the ring is limited to a reversible radial displacement, located at the level of the internal periphery of the ring, opposite the dorsal periphery, which translates into an internal diameter variation of the ring in the centrifugal or centripetal direction, according to the direction of the stress imposed on the flexible filiform element 19, indicated by one of the directions of arrow F.

The gastric ring in compliance with the invention is specifically designed to be integrated in a system of restriction and remote control of the ingestion of foodstuffs in the stomach of a patient, so as to be able to control the variation in the diameter of the ring from a distance, without any invasive surgical intervention. To this extremity, actuator 23 is an electric motor, which is ideally linked to a subcutaneous receiving circuit provided with a receiving antenna 26 (FIG. 3) for receiving a radiofrequency command and power signal, all of which is designed to be implanted in the patient's body.

As shown specifically in the figures, the electric motor is fitted to extremity 4, so that it can be brought to the outside of the ring. The electric motor is provided in the standard way with a set of bearings and gears, which are functionally linked by an electric connection 27 to the receiving antenna circuit 26.

In this preferential application, the electric motor is not provided with any internal power supply source, because its energy is provided by the receiving circuit 26, which converts radio-frequency waves received by the control unit through the external antenna into motor command signals and into energy to ensure its electrical supply. The receiving antenna 26 is adapted and chosen to receive a control and power signal at the same time.

The low energy requirement of the electric motor allows sending, by radiofrequency, control orders and activating energy to the motor, thus avoiding the need to implant an additional energy source in the body of the patient, such as a battery or battery cell.

As shown in FIGS. 3 and 4, the electric motor is linked to the receiving antenna 26 by an electric connection 27, which is protected by a protective duct 28, which ensures watertightness, and at the extremity of which is mounted said receiving circuit, which features the receiving antenna 26. The free portion, 21, of the flexible filiform element 19 is also integrated into duct 28 so as to obtain a perfectly protected assembly, watertight, and which will irritate the surrounding tissues as little as possible.

In a particularly ideal way, said antenna of receiving circuit 27 may be elastically collapsible (FIG. 3), so that the surgeon may momentarily reduce the dimensions of the implantable portion of the system, i.e. the ring, duct 28 and reception antenna circuit 26, in order to make the single piece block pass through a small-dimensioned trocar, preferably of a diameter less than, for example, 15 mm, in order to facilitate implantation.

The collapsible reception antenna circuit 26 shall be ideally but not necessarily flexible, either entirely or at least in part, and made of a flexible electric circuit, having for example the shape of a disk covered with a silicone envelope, this latter serving both for protection for the electronic components functionally connected and linked with the flexible circuit's antenna itself.

According to a particularly ideal version of the invention, the receiving circuit antenna 26 is made in one piece, for example in the shape of a collapsible disk that is noticeable like the diameter of the disk as shown in FIG. 3.

Thanks to this arrangement, and to the elastic and flexibility properties of the materials selected, it is thus possible, starting from the unfolded position of the antenna circuit 26, to collapse the antenna circuit 26 along its diameter, in order to occupy a restricted volume (FIG. 3), which allows its insertion into a trocar of circular section.

The restriction and remote control system in compliance with the invention comprises both an emitting antenna (not shown in the figures) arranged outside the patient to send a control and power signal to the receiving antenna 26. Said emitting antenna itself is linked functionally to a control interface, such as a computer or any other equivalent means available to the practicing doctor.

By using the gastric ring in compliance with the invention, implanted with its receiving circuit and antenna 26 in the unfolded position, in the body of the patient, the practicing doctor may position the emitting antenna on the skin of the patient, in the face-to-face position with the receiving antenna 26. The doctor may thus send a control and power signal in the direction of receiving antenna 26, in order to send to it, at the same time, the energy necessary to activate actuator 23, and at the same time control its direction of placement.

Thanks to the system of restriction and remote control in compliance with the invention, it is thus possible to vary the diameter of the gastric ring, without having to undertake an invasive surgical intervention, and this varying may be done at will, because multiple control cycles may be carried out at regular or irregular intervals, under the supervision of only the practicing physician.

The system shows itself, moreover, to be particularly reliable, because only the practicing physician has the control module consisting of the emitting antenna, which allows him to exercise total control over the diameter adjustment operation. The patient therefore does not have free access to any means whatsoever of adjusting the diameter of the ring.

The invention, therefore, involves a new surgical and therapeutic treatment procedure, making use of the restriction and remote control system for food ingestion in compliance with the invention, as well as a new procedure for therapeutic treatment making use of the ring-closure system in compliance with the invention.

We described previously a preferable variation of the remote-control ring, but the ring-closure system in compliance with the invention may of course be adapted to any type of surgical ring, no matter what their shape or their functionality (internal or external perimeter adjustable or not, and, if adjustable, by any means whatsoever).

The function of the surgical ring in compliance with the invention is as follows:

After installing ring 1 inside the body of the patient with the help of a trocar, the surgeon surrounds the patient's stomach with the flexible band 2 and brings the second extremity 4 and the first extremity 3 together, until the first means of stopping 16 thrusts against the rear side 7 of the means of encircling 5. The first means of stopping 16 is maintained stuck against the rear face 7, by the intrinsic elastic effect of ring 1.

The surgeon then proceeds with the effective uniting of the first and second extremities 3 and 4 of the ring, by maintaining female element 9 and taking the free extremity 11 of tab 8, which is the prehension support, in order to introduce it through orifice 9A arranged in female element 9, and to exert a pulling force on tab 8 until flexible extension 8B, which forms a cam, passes completely through the orifice, and thrusts with its stop surface 14 against the peripheral edge of orifice 9A. The passage of flexible extension 8B is made possible by the deformation flexibility of orifice 9A and said flexible extension 8B.

In the case where a re-opening of the ring becomes necessary, the surgeon holds the ring, using the second prehension support 15, and exerts a pulling and/or flexing force on the female element 9, so as to deform orifice 9A and/or said flexible extension 8B in order to retrace tab 8 out of orifice 9A. The surgeon may also then proceed with the removal of ring 1.

The invention claimed is:

1. A surgical ring (1), designed to be implanted in the body of a patient around a biological organ to form a pouch or a duct, in order to modify the cross-sectional area of a passage of the organ when it is tightened by the ring, the ring (1) comprising:
    a flexible band (2), comprising first and second extremities (3,4), the flexible band (2) being designed to be closed near these two extremities (3,4) by a closure system to form a closed ring, the said closed ring having an internal contact surface (2A) with the biological organ and an opposite external surface (2B); and
    wherein the closure system comprises a means of encircling (5) united to the first extremity (3) and arranged to evolve between:
    a de-latching configuration where the means of encircling (5) forms an open collar freeing the second extremity (4); and
    a latching configuration where the means of encircling (5) forms a closed collar designed to surround the second extremity (4) so as to unite it with the first extremity (3), the closed collar presenting opposite front (6) and rear faces (7), between which an encircling opening extends, which is designed to accept the second extremity (4),
    wherein the means of encircling (5) further comprises a male element (8) and a female element (9), each of which is mounted integrally to the first extremity (3) and mounted on or relative to the latter in such a way that, when they are connected together, the means of encircling (5) is latched, forming the closed collar, and
    wherein the second extremity (4) of the ring (1) further comprises a first means of stopping (16) designed to thrust against the rear face (7) of the closed collar surrounding the second extremity (4) of the ring in latching configuration, so as to prevent the shifting of the second extremity (4) in the opening direction of the ring (1).

2. The surgical ring (1) according to claim 1, wherein the means of encircling (5) is arranged so as to pass reversibly between the de-latching and the latching configurations.

3. The surgical ring (1) according to claim 1, wherein the female element (9) further comprises an orifice (9A) through its full thickness, between opposite first and second sides (9B, 9C), the male element (8) further comprises a tab (8) designed to be slid into orifice (9A), the tab being provided with a means of blockage (8A, 8B) which works in conjunction with orifice (9A).

4. The surgical ring (1) according to claim 3, wherein tab (8) further comprises a link extremity (10) attached to the external surface of the ring (1) and a free extremity (11), the female element (9) being likewise attached to the external surface of the ring with regard to the tab (8), in such a way as the closed collar extends towards the exterior of the ring (1).

5. The surgical ring (1) according to claim 4, wherein tab (8) further comprises a first means of support (8A), which forms a first means of blocking and is designed to act as a support against peripheral edge (13) of orifice (9A) on the first side (9B) of female element (9) and, a second means of support (8B) which forms the second means of blocking and is designed to act as a support against the peripheral edge of orifice (9A) on the second side (9C) of female element (9), the second means of support being shaped to cooperate with orifice (9A) like a cam in a bearing, the first and second means of support (8A, 8B) being arranged relative to each other so that, in latch configuration, they are tightened around the female element (9) so as to ensure a stable latching configuration.

6. The surgical ring (1) according to claim 5, wherein tab (8) further comprises a shoulder (8A), which defines a support surface forming a first means of support, and a flexible extension (8B) forming a second means of support, the free extremity (11) of tab (8) being shaped so as to act as the first prehension support, the first prehension support allowing tab (8) and flexible extension (8B) to pass through orifice (9A), so as to form the closed collar.

7. The surgical ring (1) according to claim 3, wherein tab (8) further comprises a chamfered profile to facilitate its introduction and passage into orifice (9A).

8. The surgical ring (1) according to claim 6, wherein the ring (1) further comprises a second prehension support (15) which extends near the extremity of link (10) of tab (8), the second prehension support (15) permitting holding the ring (1) during the process of separating the male (8) and female (9) elements, carried out so as to open the ring (1).

9. The surgical ring (1) according to claim 8, wherein the female element (9) features a third prehension support (9) which permits separation of male and female elements, so as to open the ring (1).

10. The surgical ring (1) according to claim 1, wherein the second extremity (4) of the ring (1) further comprises a second means of stopping (17), designed to thrust against the front face (6) of the closed collar surrounding the second extremity (4) of the ring (1) in latching configuration, so as to prevent shifting of the second extremity (4) in the closing direction of the ring (1).

11. The surgical ring (1) according to claim 10, wherein the first and second means of stopping (16, 17) are arranged relative to each other so as to tighten the closed collar (5) between them in the latching configuration, so as to substantially prevent any shifting of the second extremity (4) relative to the first extremity (3).

12. The surgical ring (1) according to claim 1, wherein flexible band (2) further comprises a portion of reduced cross-sectional area (18) at the level of the second extremity (4) of the ring (1), the portion (18) being designed to be lodged laterally in a recess (19B), of a shape complementarily arranged at the level of the first extremity (3), the recess (19) forming part of the closed collar in latching configuration, so as to ensure continuity of the internal surface (2A) of the ring (1).

13. The surgical ring (1) according to claim 12, wherein flexible band (2) further comprises a shoulder (17) at the level of the transition of the portion of reduced cross-section (18), the shoulder (17) acting as a second means of stopping.

14. The surgical ring (1) according to claim 13, wherein the flexible band (2) and the closure system (5) form a single piece made of the same material.

15. The surgical ring (1) according to claim 1, further comprising a system (19, 23, 26, 27, 28) to reversibly control the variation of an internal perimeter, the system (19, 23, 26, 27, 28) comprising a flexible filiform element (19) inserted longitudinally and by sliding into the material(24) forming the body of the ring (1), substantially between the first and second extremities (3, 4) so as to define a fixed portion (19A) united to the first extremity (3) and a free portion (21) functionally associated with an actuator (23) mounted on ring (1), such that actuator (23) can ensure reversible translation of flexible filiform element (19) as to obtain an associated variation of the diameter of the ring (1).

16. The surgical ring (1) according to claim 15, wherein actuator (23) is arranged on the ring (1) to constitute the first means of stopping (16).

17. The surgical ring (1) according to claim 1, wherein the ring is formed of a gastric ring designed to be implanted around the stomach or esophagus.

18. The surgical ring (1) according to claim 1, wherein the ring is designed to be implanted around one of the group consisting of: a bladder, a urinary tract, a gastro-intestinal tract, and a blood vessel.

19. A ring designed to be implanted in the body of a patient around a biological organ to form a pouch or a duct, the ring comprising:
 a flexible band having first and second extremities;
 a tension element slidably disposed within the flexible band;
 an actuator disposed on the second extremity of the flexible band, the actuator engaging the tension element so that operation of the actuator causes the tension element to constrict the flexible band against the biological organ; and
 a closure system having a latched configuration and a de-latched configuration, the closure system comprising a male element and a female element mounted on the first extremity, the male element configured to selectively interengage the female element to form a closed collar that encircles the second extremity of the flexible band in the latched configuration.

20. The ring of claim 19, wherein the male element is configured to reversibly interengage the female element.

21. The ring of claim 19, wherein the female element defines an orifice and the male element comprises a tab configured to pass through the orifice.

22. The ring of claim 19, wherein each of the male and female elements is joined at one extremity to an external surface of the ring.

23. The ring of claim 21, wherein tab further comprises a first surface that contacts to a first side of the female element to limit passage of the tab through the orifice, and a second surface that contacts a second side of the female element to retain the closure system in the latched configuration.

24. The ring of claim 21, wherein tab has a chamfered profile that facilitate introduction and passage of the tab through the orifice.

25. The ring of claim 19, wherein the second extremity comprises a first stop configured to abut against a rear face of the closure system in the latched configuration.

26. The ring of claim 25, wherein the second extremity further comprises a second stop configured to abut against a front face of the closure system in the latched configuration.

27. The ring of claim 26, wherein flexible band further comprises a portion of reduced cross-sectional area between the first and second stops.

28. The ring of claim 19, wherein the flexible band and the closure system are integrally formed from a single piece of material.

29. The ring of claim 19, wherein the ring is configured to be implanted around one of a patient's stomach, esophagus, bladder, urinary tract, gastro-intestinal tract or blood vessel.

* * * * *